United States Patent [19]

Clarke

[11] 4,004,239
[45] Jan. 18, 1977

[54] DISCRIMINATION CIRCUIT FOR ISOLATING DISTURBANCE SIGNALS WHICH ARE SUPERIMPOSED ON D.C. PEDESTALS

[75] Inventor: Graham Morley Clarke, Edinburgh, Scotland

[73] Assignee: Ferranti, Limited, Hollinwood, England

[22] Filed: July 18, 1975

[21] Appl. No.: 597,145

[30] Foreign Application Priority Data

July 20, 1974 United Kingdom ............ 32270/74

[52] U.S. Cl. ........................... 329/109; 307/235 C; 307/235 J; 328/151; 328/167
[51] Int. Cl.$^2$ ........................................ H03K 9/02
[58] Field of Search ................. 250/559, 562, 563; 356/237; 329/104, 109; 328/150, 151, 167; 307/235 R, 235 C, 235 J

[56] References Cited

UNITED STATES PATENTS

| | | | |
|---|---|---|---|
| 3,360,651 | 12/1967 | Linderman | 250/563 |
| 3,779,649 | 12/1973 | Bertoya et al. | 250/563 X |
| 3,825,765 | 7/1974 | Schober et al. | 250/563 |
| 3,859,537 | 1/1975 | Wolf | 250/559 |

*Primary Examiner*—Siegfried H. Grimm
*Attorney, Agent, or Firm*—Cameron, Kerkam, Sutton, Stowell & Stowell

[57] ABSTRACT

A discrimination circuit arrangement operable to discriminate between signals in the form of d.c. pedestals and superimposed thereon disturbance signals in the form of voltage variations, comprises high pass filter means to remove the d.c. pedestal, except adjacent the leading edge where a decaying impulse is produced by the filter means. A rectangular pulse is generated, triggered by the discontinuity of the pedestal and having an amplitude related to that of the pedestal; the pulse is passed through further high-pass filter means having the same time constant as the input signal filter means to produce a replica signal of the filtered input signal in the form of a decaying impulse, free of disturbance signals. The two decaying impulse signals are compared in comparison means, with a threshold signal, and disturbance signals exceeding the threshold signal produce an output signal.

10 Claims, 6 Drawing Figures

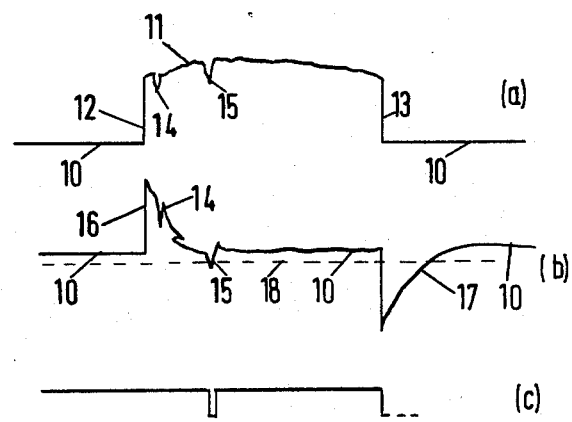
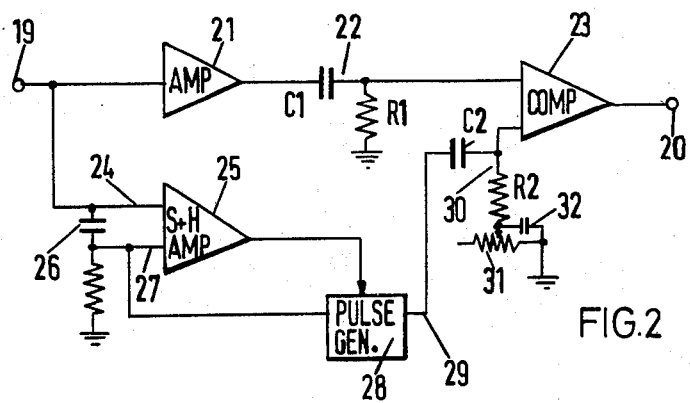
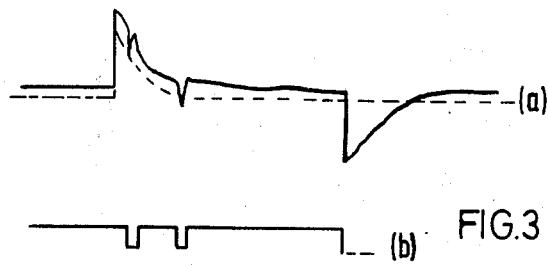
FIG.1
FIG.2
FIG.3

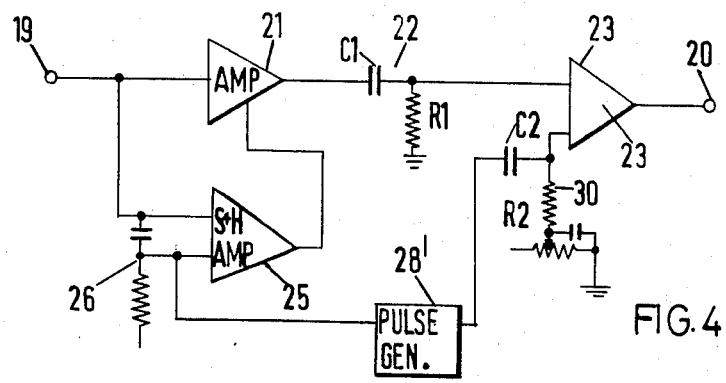
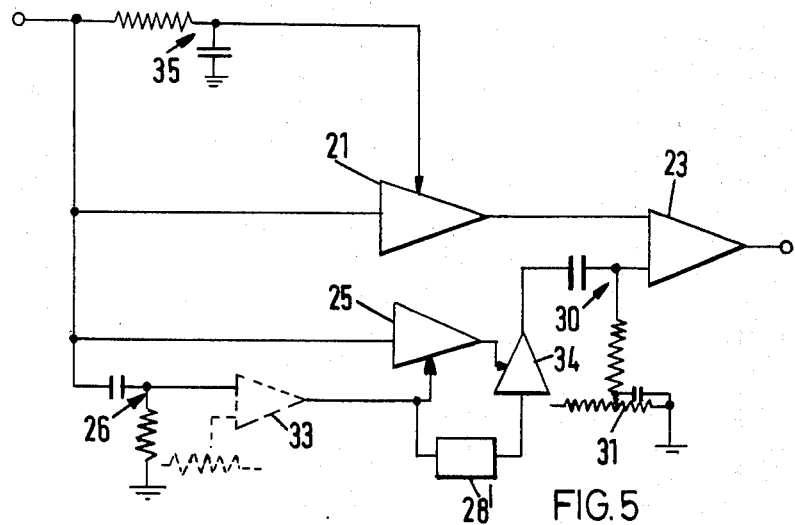
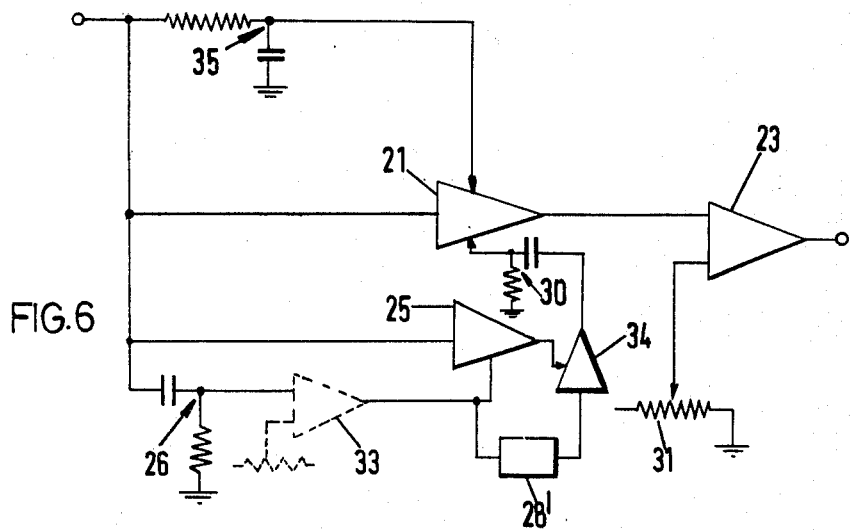

DISCRIMINATION CIRCUIT FOR ISOLATING DISTURBANCE SIGNALS WHICH ARE SUPERIMPOSED ON D.C. PEDESTALS

This invention relates to discrimination circuit arrangements and in particular to discrimination circuit arrangements operable to discriminate between signals in the form of d.c. pedestals and superimposed thereon disturbance signals in the form of voltage variations.

Such discriminations circuits are particularly suitable for use with a surface scanning fault detector of the type in which a beam of optical radiation is caused to scan repetitively across the surface of a moving web transversely to the direction of web motion, radiation reflected from the surface being collected and applied to a photodetector such that any change in the level of radiation collected due to a surface fault causes a disturbance in an output signal to be produced by the photodetector. Such surface scanning fault detectors will hereinafter be referred to as being "of the type described". If the width of the moving web is less than the scan length then the edges of the web can produce discontinuities in the photodetector output signal such that is appears as a series of d.c. pedestal signals having superimposed thereon fault signals in the form of voltage disturbances. In order to evaluate the fault signals it is necessary to discriminate between the fault signals and the pedestal signals.

Methods previously employed to discriminate between the disturbances and the pedestal signals have consisted either of attempting to remove the d.c. component on the pedestal by high pass filtering or of producing a disturbance-free pedestal and subtracting it from the input signal.

In the first mentioned method filtering of the edges of each pedestal results in a remanent d.c. signal in the form of a decaying impulse adjacent the edges and upon which disturbances may be masked.

The second mentioned method is described in British patent specifications Nos. 1,303,041 and 1,303,042 in which the input signal is passed through a filter network which assumes a high-pass characteristic to pass the edges and thereafter assumes a low-pass characteristic to remove the disturbance signals, resulting in a disturbance-free pedestal signal for subtraction. However, any disturbance immediately adjacent to the edges is passed by the filter in its first characteristic state and completely eliminated with the pedestal by the subsequent subtraction.

It is an object of the present invention to provide an improved discrimination circuit of simple construction able to discriminate between signals in the form of d.c. pedestals and disturbance signals superimposed thereon immediately adjacent the leading edges of the pedestals.

According to one aspect of the present invention a discrimination circuit arrangement comprises an input terminal arranged to receive an input signal in the form of d.c. pedestal signals on which disturbance signals may be superimposed, input signal filter means operable to remove the d.c. components of each pedestal signal except immediately adjacent to the leading edge thereof, signal generating means responsive to the leading edge of each pedestal signal to generate a replica signal having the amplitude and shape of the remaining d.c. components of the filtered pedestal signal and control means responsive to the replica signal to eliminate the remaining d.c. components of each pedestal signal.

According to another aspect of the present invention a surface scanning fault detector of the type stated includes a discrimination circuit arrangement as defined in the preceding paragraph.

The invention, employed as part of a surface scanning fault detector of the type described, will now be described by way of example with reference to the accompanying drawings, in which:

FIG. 1 at (a), (b) and (c) shows waveforms of signals produced by known apparatus during the discrimination of disturbances on a discontinuous background signal, FIG. 2 is a discrimination circuit arrangement according to the present invention, FIG. 3 at (a) and (b) shows waveforms of signals produced by the circuit arrangement of FIG. 2, FIG. 4 is an alternative form of the discrimination circuit arrangement of FIG. 2, and FIGS. 5 and 6 are further alternative forms of discrimination circuit arrangements.

Referring to FIG. 1, the waveform shown at (a) is that of a typical electrical output signal for one scan of a surface scanning fault detector (not shown). This signal comprises a background level signal 10 produced when the beam is not incident upon the surface, which signal level increases to that at 11 by a discontinuity 12 when the beam crosses the leading edge of the surface. The signal 11 at a higher background level is produced as the beam crosses the surface, returning to the lower background level 10 by a discontinuity 13 at the trailing edge of the surface. The positive-going d.c. voltage 'pedestal' of the background signal is indicative of a normally reflecting surface and any light absorbing faults in the surface appear as negative going disturbances 14 and 15. It will also be appreciated with reference to FIG. 1(a) that the level of light reflected in the absence of faults varies throughout the scan, falling in level towards each end, so that the background signal is subject to the combination of a low frequency variation throughout the scan, discontinuities at the leading and trailing edges of the surface, and disturbances due to faults in the surface.

In known circuit arrangements for discriminating the disturbances 14 and 15, signal processing has comprised differentiating the signal in a simple resistor-capacitor high-pass filter (not shown). The waveform of the signal after filtering is shown in FIG. 1(b) with the same time scale as that of FIG. 1(a) and discontinuities 12 and 13 in the level of the background signal are replaced by the impulses 16 and 17 respectively. These impulses decay exponentially to the background level 10, and high frequency disturbances 14 and 15 are present on the modified signal. As the background signal 10 is at a constant level (apart from the decaying impulses) the signal voltage is compared with a threshold voltage, shown by a broken line 18 in FIG. 1(c), in a differential amplifier. Disturbances appearing away from the impulse, such as 15, cross the threshold and produce a change in output state of the amplifier shown by the waveform in FIG. 1(c) of the output signal. The disturbance 14 which occurs on the decaying part of the impulse 16 does not cross the threshold and does not cause a change in the output signal of the amplifier. The negative going impulse 17 marks the end of the scan for which detection of faults is required so the impulse 17 may be used to switch off the arrangement and prevent the impulse and any subsequent disturbances having effect.

It will be appreciated that the decaying part of the impulse 16 has comprised an unusuable part of the signal and the duration of this part is dependent upon the time constant of the high-pass filter network employed to remove the variations in amplitude of the pedestal 11. Adequate filtering of the low frequency variation requires a network having a large time-constant whereas discrimination of disturbances adjacent the discontinuity 12 requires a small time constant, and a compromise is chosen betwen the two extremes.

This problem is overcome by the discrimination circuit arrangement of the present invention shown in one embodiment in FIG. 2. The circuit arrangement comprises an input terminal 19 and an output terminal 20. The input terminal 19 is connected to input signal filter means comprising input signal amplifier 21 serially connected with a first resistor-capacitor high-pass filter network 22. The filter network comprises a capacitor C1 in series with the signal and a resistor R1 connected between the capacitor and earth. The input signal filter means is connected to one input terminal of control means comprising means 23, the output terminal of which comprises the circuit output terminal 20.

The circuit input terminal 19 is also connected to signal generating means, that is to a first input terminal 24 of a sample-and-hold amplifier 25 and, by way of a subsidiary high-pass filter 26 (of shorter time constant then the network 22) to a second input terminal 27 of the amplifier 25. The filtered signal, appearing at the input terminal 27, comprises a trigger signal used to trigger a pulse generator 28. The generator 28 is operable to produce at an output terminal 29 a pulse having an amplitude determined by a level signal, produced by the sample-and-hold circuit 25 and a duration in excess of the time between the discontinuities 12 and 13.

The terminal 29 is connected by way of further filter means, comprising a second high-pass filter network 30 of a capacitor C2 and resistor R2, to a second input terminal of the comparison means 23. The terminal of the resistor R2 remote from the capacitor C2 is connected to a source of threshold bias voltage by way of a potentiometer 31 which potentiometer enables the bias voltage to be set to a predetermined level. A bypass capacitor 32 prevents the resistance of the potentiometer from modifying the time constant of the filter network. The time constant of the first and second filter networks are identical.

Operation of the circuit arrangement is described with reference to the waveforms of FIGS. 3(a) and 3(b).

The input signal applied to the input terminal 19 has a waveform corresponding to that shown in FIG. 1(a). The signal is amplified in the amplifier 21, filtered by the network 22 and applied to one input terminal of the comparison means 23. The waveform of the filtered signal appearing at the input terminal of the comparison means is shown in solid lines in FIG. 3(a) and corresponds with that shown in FIG. 1(b) for a conventional arrangement.

A portion of the input signal is applied to the sample-and-hold amplifier 25 which produces a "level" signal having a d.c. level related to the amplitude of the discontinuity of the signal due to the leading edge of the surface being scanned. The level signal controls the amplitude of the pulse generated by the pulse generator 28 which pulse is triggered by the signal discontinuity 12 after being formed into an impulse by the filter network 26. The generated pulse is reshaped by the filter network 30 of the further filter means and provides a replica signal of the leading edge of the pedestal signal in the form of an impulse having an amplitude and decay time signal equal to that of the pedestal signal filtered by the network 22.

The replica signal applied to the other input terminal of the comparison means thus has the waveform shown by the broken line in FIG. 3(a) and is offset in amplitude from the filtered input signal by the threshold bias signal level determined by the potentiometer 31. This comparison signal conforms closely with the signal but is "clean", that is, has no amplitude disturbances such as 14 or 15.

It will be appreciated from FIG. 3(a) that the disturbance 14, provided it is of greater amplitude than the threshold level, is capable of crossing the threshold signal on the decaying part of the impulse to the same extent as the disturbance 15 occurring later in the scan, and of causing a comparison means output signal to change level as illustrated by the waveform of FIG. 3(b). The pulse generator 28 produces a positive-going unipolar pulse for filter network 30 and, as will be seen from FIG. 3(a) the impulse derived from it does not provide a suitable comparison level for the impulse 17 due to the trailing edge discontinuity 13.

In the particular application of a surface inspection device the arrangement is not required to take account of the trailing edge as the discrimination of disturbances is no longer required once the trailing edge is reached. As stated previously the occurrence of the trailing edge discontinuity may be used to disable processing circuitry until the commencement of the next scan. The trailing edge may have to be detected to perform such an action but if the total number of disturbances discriminated is being counted then the effect of the trailing edge may be nullified by the subtraction of 'one' from the number of disturbances discriminated in each scan. Alternatively, because the present invention permits the discrimination of disturbances appearing immediately after the leading edge discontinuity it is possible to employ an additional scanning arrangement of the opposite sense wherein neither arrangement scans a trailing edge and both edges are treated as leading edges, after which disturbances are discriminated as described above.

An alternative form of the circuit arrangement of FIG. 2 is shown in FIG. 4. In this arrangement the pulse generator 28' is operable to produce a pulse of constant amplitude and the level signal of the sample-and-hold amplifier 25 is used to control the gain of the amplifier 21 of the input signal filter means, thereby modifying the input signal so that the amplitude of each discontinuity of the signal is made equal to the amplitude of the generated pulses. The leading edge of a discontinuity is still used to trigger the generator 28'.

In the arrangement shown in FIG. 4 the effect of controlling the gain of the amplifier 21 by means of the low frequency variation in the background signal is that if the gain is changed to accommodate a new value of discontinuity the amplitude of disturbances on the signal will be altered; if the gain change is larger the disturbance signals may not have sufficient amplitude to trigger the comparator when they would otherwise do so.

Such an occurrence may be prevented by the circuit arrangement shown in FIG. 5 which also employs an alternative form of input signal filter means. In this Figure components common to other Figures are given the same reference numerals and the alternative form of signal filter means may be employed in the circuit arrangement of FIGS. 2 and 4. The input signal is fed by way of an amplifier 21 comprising part of the input signal filter means into the comparison means 23. The signal is also passed to signal generating means, that is to a sample-and-hold amplifier 25 and a subsidiary filter 26. The signal from the subsidiary filter is also used to trigger a pulse of constant amplitude in pulse generator 28' by way of threshold detection means 33 to ensure that only the relatively large discontinuities cause a pulse to be produced. The output of the pulse generator is connected to an amplifier 34, the gain of which is controlled by the level signal from the sample-and-hold amplifier 25. The output of the amplifier 34 is connected by way of the high-pass filter network 30 of the further filter means to the comparison means 23. The input signal also passes through a low-pass filter network 55, having the same time constant as the network 30 and forming part of the input signal filter means; the output of the filter network 35 is connected to control the gain of the amplifier 21.

In operation the signal is filtered by network 35 which produces a signal "cleaned" of the discontinuities and slow to change in amplitude after the discontinuities. This filtered signal controls the gain of signal amplifier 21 to flatten its response everywhere but at the discontinuities so that the amplifier output signal has a waveform similar to that shown in FIG. 1(b). The signal has effectively been differentiated but the amplitudes of the disturbances are not affected. The signal removed of its low frequency components by the differentiation is fed to the comparator with a replica of the decaying impulses of the differentiated discontinuity. The replica may be produced as described with reference to FIG. 2 or with the optional comparator 33 described above. Alternatively, as shown by the circuit arrangement of FIG. 6 the pulse, differentiated by the further filter means, may be used in addition to the filter network 35 to control the gain of the signal amplifier 21 of the input signal filter means. In this case the comparison means 23 is supplied with a threshold bias signal at a predetermined level by potentiometer 31.

The component values of C1 and C2 are equal as are the values of R1 and R2. Apart from providing identical time constants for the two filter networks, the identity of component values means that they are equally affected by stray capacitances and impedances and continue to have equal time constants.

As stated the circuit arrangements of FIGS. 2 to 6 have been described with reference to a surface inspection system where the background signal comprises a series of discontinuities occurring at normally constant fixed intervals. The nature of the signal obtained and applied to the circuit arrangement is such that there is little or no possibility of disturbances appearing other than superimposed upon the part 11 of the signal between two discontinuities. The circuit arrangements are capable of discriminating such disturbances and discontinuities of differing amplitudes but in the forms described are not equipped to deal with a negative-going discontinuity 13 in FIG. 1(a) that is, a return from the level 11 to that 10. The circuit arrangements may be readily modified to detect such discontinuities by the addition of a negative going pulse generator (not shown) in parallel with the pulse generator 28 (or 28') and triggered by a negative-going impulse from the filter 26; or by adapting the pulse generator 28 (or 28') to produce a pulse upon being triggered by a positive going impulse from the filter network 26, the pulse being terminated by a subsequent negative-going impulse. It will also be appreciated with such arrangements that it may be necessary to arrange for pulses to be generated by the or each generator 28 (or 28') in response to an impulse of a predetermined minimum amplitude so that disturbances appearing on the signal do not trigger the pulse genertor 28.

The comparators in the above embodiments are shown as employing a threshold which is negative with respect to the background signal level, but the arrangements could employ a positive threshold level by connecting the potentiometer 31 to a source of positive potential.

Provision may also for both positive and negative thresholds enabling both positive-going and negative-going disturbances to be detected, although this may be achieved by duplication of the discriminator circuit arrangements shown (but with thresholds of different polarity) so that output signals due to different disturbance sense could be segregated.

What I claim is:

1. A discrimination circuit arrangement comprising an input terminal arranged to receive an input signal in the form of d.c. pedestal signals on which disturbance signals may be superimposed, input signal filter means operable to remove the d.c. components of each pedestal signal except immediately adjacent to the leading edge thereof, signal generating means responsive to the leading edge of such pedestal signal to generate a replica signal having the amplitude and shape of the remaining d.c. components of the filtered pedestal signal, and control means responsive to the replica signal and to the filtered pedestal signal to eliminate the remaining d.c. components of each filtered pedestal signal, said disturbance signals being obtained at the output of the control means.

2. A discrimination circuit arrangement as claimed in claim 1 in which the input signal filter means comprises in series an amplifier and a high-pass filter network arranged to receive an input signal from the input terminal.

3. A discrimination circuit arrangement as claimed in claim 1 in which the input signal filter means comprises an amplifier arranged to receive an input signal from the input terminal, and a low-pass filter network arranged also to receive the input signal, the output signal of the filter network being operable to control the gain of the amplifier.

4. A discrimination circuit arrangement as claimed in claim 3 in which the control means comprises the amplifier of the input signal filter means, said amplifier having its gain controlled by the replica signal so as to pass only disturbance signals super-imposed on the pedestal signal, and comparison means arranged to compare the disturbance signals with a threshold bias signal of predetermined amplitude and to provide an output signal when the amplitude of a disturbance signal differs from the amplitude of the replica signal by an amount in excess of the level of the threshold bias signal.

5. A discrimination circuit as claimd in claim 1 in which the signal generating means comprises subsidiary high-pass filter means responsive to the leading edge of the pedestal signal to produce a trigger signal in the form of a decaying impulse, means operable to generate a level signal having an amplitude related to that of the pedestal signals, pulse generating means responsive to each trigger signal to generate a rectangular pulse coincidentally with the leading edge of the pedestal signal, the amplitude of the pulse being controlled by the level signal, and further filter means having a time constant equal to that of the input signal filter means operable to filter the leading edge of the rectangular pulse to provide the replica signal.

6. A discrimination circuit arrangement as claimed in claim 5 in which the pulse generating means comprises a pulse generator operable to generate a pulse of a predetermined amplitude and an amplifier of the pulse, the gain of which amplifier is controlled by the amplitude of the level signal.

7. A discrimination circuit arrangement as claimed in claim 5 in which the signal generating means includes threshold detection means operable to inhibit the passage of trigger signals below a predetermined threshold level, said level being set to exclude trigger signals formed other than by the leading edge of the pedestal signal.

8. A discrimination circuit arrangement as claimed in claim 1 in which the signal generating means comprises high-pass filter means responsive to the leading edge of the pedestal signal to produce a trigger signal in the form of a decaying impulse, pulse generating means responsive to each trigger signal to generate a rectangular pulse of predetermined amplitude coincidentaly with the leading edge of the pedestal signal, means operable to generate a level signal having an amplitude related to that of the pedestal signal and connected to the input signal filter means to control the amplitude of the filtered pedestal signal in relation to the amplitude of the rectangular pulse, and further filter means having a time constant equal to that of the input signal filter means operable to filter the leading edge of the rectangular pulse to provide the replica signal.

9. A discrimination circuit arrangement as claimed in claim 8 in which the signal generating means includes threshold detection means operable to inhibit the passage of trigger signals below a predetermined threshold level, said level being set to exclude trigger signals formed other than by the leading edge of the pedestal signal.

10. A discrimination circuit arrangement as claimed in claim 1 in which the control means comprises a signal comparison means arranged to receive as input signals the filtered input pedestal signal and any disturbances superimposed thereon, the replica signal and a threshold bias signal of predetermined level, the signal comparison means being operable to provide an output signal when the amplitude of the filtered input signal differs, by reason of superimposed disturbance signals, from the amplitude of the replica signal by an amount in excess of the level of the threshold bias signal.

* * * * *